United States Patent [19]

Lacroix et al.

[11] Patent Number: 5,453,551
[45] Date of Patent: Sep. 26, 1995

[54] PURIFICATION OF PENTAFLUOROETHANE

[75] Inventors: Eric Lacroix, Lyons; André Lantz, Vernaison; Bernard Cheminal, Brignais, all of France

[73] Assignee: Elf Atochem S.A., Puteaux, France

[21] Appl. No.: 197,985

[22] Filed: Feb. 17, 1994

[30] Foreign Application Priority Data

Feb. 24, 1993 [FR] France .................... 93 02119

[51] Int. Cl.⁶ .................................... C07C 17/38
[52] U.S. Cl. ................ 570/177; 570/168; 570/169
[58] Field of Search ...................... 570/168, 169, 570/177

[56] References Cited

U.S. PATENT DOCUMENTS 3,755,477  8/1973  Firth et al. .................. 510/169
4,158,675  6/1979  Potter.
5,087,329  2/1992  Felix.

FOREIGN PATENT DOCUMENTS

0508631A1  10/1992  European Pat. Off. .
2381006    9/1978   France .

Primary Examiner—Alan Siegel
Attorney, Agent, or Firm—Morgan & Finnegan

[57] ABSTRACT

The invention relates to the purification of pentafluoroethane (F125) containing chloropentafluoroethane (F115).

The F-125-F115 mixture to be purified is subjected to a fluorination stage to convert F115 into hexafluoroethane (F116) which is then separated from F125, for example by distillation.

10 Claims, No Drawings

PURIFICATION OF PENTAFLUOROETHANE

The invention relates to the purification of pentafluoroethane (F125) containing chloropentafluoroethane (F115).

The F125–F115 mixture to be purified is subjected to a fluorination stage to convert F115 into hexafluoroethane (F116) which is then separated from F125, for example by distillation.

FIELD OF THE INVENTION

The present invention relates to the purification of pentafluoroethane (F125 hereinafter) containing chloropentafluoroethane (F115) and its subject is more particularly a purification process consisting in subjecting a F125–F115 mixture to fluorination conditions such that F115 is converted to hexafluoroethane (F116).

BACKGROUND OF THE INVENTION

F125 is an HFC (hydrofluorocarbon) which can be employed as substitute for F115 (a CFC or chlorofluorocarbon) in the field of low-temperature refrigeration.

Known processes for obtaining F125 include, inter alia, the fluorination of perchloroethylene or its fluorinated derivatives like 1,1-difluoro-1,2,2-trichloroethane (F122), 1,1-dichloro-2,2,2-trifluoroethane (F123) and 1-chloro-1,2,2,2-tetrafluoroethane (F124), the fluorination of chlorotrifluoroethylene (F1113) or the chemical reduction of F115, especially the hydrogenolysis of the latter. In most cases these synthesis routes to F125 produce a crude F125 which is contaminated by significant quantities (several hundred ppm to several tens per cent) of F115, either through formation of byproducts due to the high temperatures needed to obtain high yields of F125 (in the case of fluorination reactions), or because of nonquantitative conversions of the starting material (in the case of the hydrogenolysis of F115).

As indicated in U.S. Pat. No. 5,087,329, the separation of the compounds F125 and F115 by distillation is very difficult, or even impossible if it is desired to obtain a very low F115 content.

Nevertheless, there is at present a trend towards a commercial F125 of high purity in which the F115 content might be of the order of a hundred ppm or so. Because of the difficulties encountered in separating the compounds F125 and F115, obtaining such low F115 contents does not appear to be feasible with a distillation line of realistic size. Processes for purifying F125 which make it possible to gain access to these very low F115 contents are therefore being investigated at present.

The process for separating F125 and F115 which is described in the abovementioned U.S. Pat. No. 5,087,329 relies on extractive distillation consisting in adding to the F125-F115 mixture before distillation an extractant consisting of an optionally hydrogenated and/or chlorinated $C_1$–$C_4$ fluorinated hydrocarbon which has a boiling point of between −39° C. and +50° C. As examples of such extractants the patent mentions 1,2-dichlorotetrafluoroethane (F114), 1,1-dichlorotetrafluoroethane (F114a), 1,1,2-trichlorotrifluoroethane (F113), 1,1,1-trichlorotrifluoroethane (F113a), 2-chloro-1,1,1,2-tetrafluoroethane (F124), 2,2-dichloro-1,1,1-trifluoroethane (F123), trichlorofluoromethane (F11) and octafluorocyclobutane (F-C318).

In Patent Application EP 508,631, which describes the production of HFC compounds by liquid-phase chemical reduction of chlorinated, brominated or iodinated compounds with a metal hydride or a complex of such a hydride, it is indicated that this process may be of interest for purifying certain HFCs like F125. The purification of F125 is not exemplified. On the other hand, example 6 describes the reduction of F115 with $LiAlH_4$ in diglyme; the best result indicates a 60% conversion of F115 to F125.

DESCRIPTION OF THE INVENTION

It has now been found that it is possible to fluorinate an F125–F115 mixture to convert F115 to F116 with a good conversion, practically without affecting F125. Consequently, a simple distillation of the F116 formed makes it possible to gain access to an F125 containing only a few hundred ppm of F115.

The subject of the present invention is therefore a process for purifying F125, characterized in that it consists in subjecting the F125–F115 mixture to be purified to a fluorination and then separating off the F116 formed.

Any known method of fluorination allowing F115 to be converted to F116 without degrading excessive quantities of F125 can be used to carry out the first stage of the purification process according to the invention.

Since the fluorination of F115 to F116 is relatively difficult, it requires severe means of fluorination. Although it is possible to operate in a liquid phase with powerful fluorination agents such as $SbF_5$, it is preferred to make use of a gas-phase catalytic fluorination with HF, which has the advantage of being easily capable of being industrialized and of being applicable to a continuous process, without requiring excessively frequent regenerations or changes of the catalyst charges.

The catalyst employed for the gas-phase fluorination may be chosen from all bulk or supported catalysts known to a person skilled in the art for fluorination of this type. Without any limitation being implied, the following may be mentioned more particularly:

- chromium-, nickel- and/or magnesium-based catalysts supported on a material compatible with hydrofluoric acid, such as, for example, charcoal, alumina and aluminium trifluoride,

- bulk catalysts such as alumina, chromium derivatives, in particular a chromium(III) oxide, or mixed catalysts based on chromium and another constituent, such as, for example, nickel, magnesium or zinc.

In making use of the process according to the invention more particular preference is given to bulk $Cr_2O_3$ catalysts, bulk Ni-Cr catalysts as described in Patent Application FR 9115228, the content of which is incorporated here by reference, and mixed catalysts based on nickel and chromium oxides, halides and/or oxyhalides deposited on a support consisting of aluminium fluoride or of a mixture of aluminium fluorides and alumina. This last type of catalyst is described in Patent Application FR 2,669,022, the content of which is incorporated here by reference.

In the case of a given catalyst the operating conditions of the gas-phase fluorination of the F125–F115 mixture to be purified depend on the desired target in respect of residual F115 and are generally the following:

a) The reaction temperature is generally between 300 and 600° C.; the higher it is, the higher the conversion of F115. However, since excessively high temperatures may give rise to a considerable decomposition of F125 and may also be prejudicial to catalyst lifetime, the preferred temperature range is between 350 and 550° C., and more particularly between 380 and 480° C.

b) The contact time, calculated as being the flow time of the gases (under reaction conditions) through the volume of randomly packed bulk catalyst is between 3 and 300 seconds and more particularly between 15 and 200 seconds. Here too, it must be adjusted as a function of the residual F115 target sought after. An increase in this contact time lowers the residual F115 concentrations but, on the other hand, the volumes of F125 which are treated are smaller and generally the interfering F125 degradation reactions are slightly increased. In contrast to temperature, this parameter has little influence on catalyst deactivation; consequently, the operating margin in respect of this parameter is wider and an optimization of this contact time makes it possible to arrive at the best compromise between residual F115 content and plant production efficiency.

c) The HF flow rate–expressed as the HF/organics (F125+F115) molar ratio for practical reasons–depends on the proportion of F115 in the crude to be treated. This molar ratio affects the purified final product (F115 content), but also the stability of the F125 and, indirectly, the catalyst lifetime. It may be between 0.05 and 20. A good compromise between a high F115 conversion and reasonable quantities of unreacted HF reduces this bracket to the values 0.5 to 10. A molar ratio of between 0.6 and 5 will be preferably employed.

d) Under operating conditions liable to foul the catalyst [low molar ratio, high temperatures (>500° C.)] it may be judicious to introduce a low content of oxygen with the reactants. Depending on the operating conditions, this content may vary between 0.02 and 5% relative to the organic reactants (molar percentage). The purpose of this oxidizing agent is to react with the "heavies" which give rise to the fouling of the catalyst.

e) The fluorination reaction according to the invention may be conducted at atmospheric pressure or at a pressure above the latter. For practical reasons the operation will be generally carried out in a range extending from 0 to 25 bars gauge.

f) The materials employed for the construction of the plant must be compatible with the presence of hydrogen acids such as HCl and HF; they may be chosen from "Hastelloy" or "Inconel" which stand up to the corrosive media containing these hydrogen acids.

g) Depending on the target sought after, especially to reach F115 contents of the order of a hundred ppm or so, it may be found useful to employ several reactors in series.

After the fluorination stage the F116 formed and any byproducts (trifluoromethane, CO, $CO_2$) can be easily separated from F125, for example by simple distillation, since their boiling points are very far away from that of F125.

Although the process according to the invention can be applied to F125–F115 mixtures with high F115 contents (for example up to 30%), it is intended more particularly for the purification of a crude F125 in which the molar content of F115 does not exceed 10%. Furthermore, this crude F125 to be purified may also contain small proportions of the byproducts resulting from its synthesis (F123, F124, F143a, F134a, HCl, etc.).

The use of the process according to the invention makes it possible to obtain commercial F125 of very high purity with a residual F115 content reduced, in some cases, to about a hundred ppm. The gas-phase fluorination enables this degree of purity to be obtained while employing continuously operating industrial plants; however, in some cases, variants such as liquid-phase fluorinations may be found more suited to this problem of F125 purification.

The following examples illustrate the invention without limiting it.

EXAMPLE 1

1A - CATALYST PREPARATION AND ACTIVATION

In a rotary evaporator were placed 250 ml of a support containing, by weight, 73% of aluminium fluoride and 27% of alumina, obtained in a preceding stage by fluorination of Grace HSA alumina in a fluidized bed at about 300° C. with the aid of air and hydrofluoric acid (volume concentration of 5 to 10% of this acid in the air). The starting Grace HSA alumina exhibited the following physical chemical characteristics: .

- form: beads 1–2 mm in diameter
- BET surface: 220 $m^2/g$
- pore volume: 1.2 $cm^3/g$ (for pore radii of between 4 nm and 63 μm)
- sodium content: 600 ppm.

Two separate aqueous solutions were also prepared (a) chromic solution containing

| | |
|---|---|
| chromic anhydride: | 57 g |
| water: | 41 g |

(b) methanolic solution containing:

| | |
|---|---|
| methanol: | 81 g |
| water: | 18 g |

The mixture of these two solutions was then introduced, at ambient temperature, atmospheric pressure and over approximately 45 minutes, onto the support, with stirring. The catalyst was then dried for 4 hours in a stream of nitrogen in a fluidized bed at about 110° C.

100 ml (95 g) of dry catalyst were charged into a tubular reactor made of Inconel with an internal diameter of 27 mm and the temperature was raised to 120° C. under a stream of nitrogen at atmospheric pressure. This treatment was maintained for about ten hours and the nitrogen was then gradually replaced with hydrofluoric acid, care being taken that the increase in temperature did not exceed 95° C. and, when an $HF/N_2$ molar ratio of 50/50 was reached, the temperature was raised to 300° C.

After disappearance of the exothermic peaks the temperature was raised to 350° C. under a stream of pure hydrofluoric acid (1mole/hour) for 6 hours.

The catalyst was finally purged in a stream of nitrogen before the catalysis test is commenced. The characteristics of catalyst A dried and activated in this way were as follows:

| chemical composition (by weight) | |
|---|---|
| fluorine: | 52.0% |
| aluminium: | 22.0% |
| chromium: | 14.9% |
| oxygen: | 11.1% (remainder to 100) |

-continued

| physical properties: | |
|---|---|
| BET surface: | 22.7 m²/g |
| volume of pores with a radius of between 4 nm and 63 μm: | 0.38 cm³/g |
| surface of the pores of radius greater than 4 nm: | 21.9 m²/g |

1B - FLUORINATION OF F115 IN AN F125–F115

The performance of catalyst A in the fluorination of F115 present in a crude F125 was tested at atmospheric pressure, without oxygen addition, under operating conditions and with the results collated in Table 1, which follows.

The initial crude F125 was 98.35% pure (mol %), the major impurities being F115 (1.54%) and F124 (550 ppm).

TABLE 1

| TEST No. | 11 | 12 | 13 |
|---|---|---|---|
| Operating conditions | | | |
| Temperature (°C.) | 450 | 450 | 500 |
| HF/F115 + F125 molar ratio | 1 | 1.1 | 0.9 |
| Contact time (a) | 18.3 | 33.4 | 16.9 |
| Age of the catalyst (h) | 23 | 47 | 67 |
| Results | | | |
| Overall degree of conversion of F115 (%) | 56.5 | 72.7 | 59.1 |
| Selectivity for F116 (%) | ~100 | ~100 | ~100 |
| Overall degree of conversion of F125 (%) | 0.14 | 0.16 | 0.3 |
| F115 content in purified F125 (mol %) | 0.67 | 0.42 | 0.63 |

The byproducts formed and identified, after neutralizing the acids (HF and HCl) by washing, were F23 ($CF_3H$) and $CO/CO_2$.

EXAMPLE 2

A catalyst B was prepared, based on nickel and chromium which were deposited on $AlF_3$. The procedure was as in Example 1A, but using the following two aqueous solutions:

(a) chromic solution with added nickel chloride, containing:

| chromic anhydride: | 12.5 g |
|---|---|
| nickel chloride hexahydrate: | 29 g |
| water: | 42 g |

(b) Methanolic solution containing:

| methanol: | 18 g |
|---|---|
| water: | 33 g. |

After drying and activation the characteristics of catalyst B were as follows:

| Chemical composition (by weight) | |
|---|---|
| fluorine: | 64.4% |
| aluminium: | 27.2% |
| nickel: | 3.8% |
| chromium: | 3.3% |
| oxygen: | 1.3 % (remainder to 100) |
| Physical properties: | |
| BET surface: | 35.4 m²/g |
| volume of pores with a radius of between 4 nm and 63 μm: | 0.47 cm³/g |
| surface of pores of radius greater than 4 nm: | 32.8 m²/g. |

The operating conditions and the results obtained with this catalyst B in the fluorination, at atmospheric pressure, of F115 present in the same crude F125 as in Example 1B are collated in Table 2, which follows.

TABLE 2

| TEST No. | 21 | 22 | 23 |
|---|---|---|---|
| Operating conditions | | | |
| Temperature (°C.) | 450 | 450 | 500 |
| HF/F115 + F125 molar ratio | 0.9 | 1 | 1 |
| Contact time(s) | 19.9 | 35.5 | 18.1 |
| Age of the catalyst (h) | 24 | 48 | 72 |
| Results | | | |
| Overall degree of conversion of F115 (%) | 64.3 | 80.5 | 39.6 |
| Selectivity for F116 (%) | 95 | 94 | 98 |
| Overall degree of conversion of F125 (%) | <0.1 | <0.1 | 0.2 |
| F115 content in purified F125 (mol %) | 0.55 | 0.3 | 0.93 |

As in Example 1A, the byproducts formed identified after washing were F23 ($CF_3H$) and $CO/CO_2$.

EXAMPLE 3

A catalyst C according to the invention was prepared in which the chromium and nickel contents were substantially double those in catalyst B. The procedure was as in Example 1A but employing the following two aqueous solutions:

(a) chromic solution with added nickel chloride, containing:

| chromic anhydride: | 25 g |
|---|---|
| nickel chloride hexahydrate: | 58 g |
| water: | 40 g |

(b) methanolic solution containing:

| methanol: | 35 g |
|---|---|
| water: | 30 g. |

After drying and activation the characteristics of catalyst C were as follows:

| Chemical composition (by weight) | |
|---|---|
| fluorine: | 58.5% |
| aluminium: | 25.1% |
| nickel: | 6.8% |
| chromium: | 5.6% |
| Physical properties: | |
| BET surface: | 15.1 m²/g |
| volume of pores with a radius of between 4 nm and 63 μm: | 0.382 cm³/g |
| surface of pores of radius greater than 4 nm: | 18 m²/g. |

The operating conditions and the results obtained with this catalyst C in the fluorination, at atmospheric pressure, of the same crude F125 as in Example 1B are collated in Table 3, which follows.

TABLE 3

| TEST No. | 31 | 32 | 33 | 34 | 35 |
|---|---|---|---|---|---|
| Operating conditions | | | | | |
| Temperature (°C.) | 450 | 450 | 450 | 450 | 430 |
| HF/F115 + F125 molar ratio | 1 | 1.1 | 1.2 | 0.8 | 0.6 |
| Contact time(s) | 25 | 101 | 103 | 100 | 107 |
| Age of the catalyst (h) | 24 | 48 | 94 | 118 | 190 |
| Results | | | | | |
| Overall degree of conversion of F115 (%) | 87 | 98.2 | 99.4 | 97.7 | 96.8 |
| Selectivity for F116 (%) | ~100 | ~100 | ~100 | ~100 | ~100 |
| Overall degree of conversion of F125 (%) | <0.1 | 0.2 | 0.2 | 0.25 | 0.4 |
| Molar content of F115 in purified F125 | 0.2% | 270 ppm | 100 ppm | 350 ppm | 600 ppm |

The byproducts formed and identified after washing were the same as in Examples 1 and 2.

EXAMPLE 4

A bulk catalyst was employed, based on chromium oxide activated in the following manner:

100 ml (134 g) of chromium(III) oxide were charged into a tubular reactor made of Inconel with an internal diameter of 27 mm and the temperature was raised to 120° C. under a stream of nitrogen at atmospheric pressure. This treatment was maintained for about 10 hours and the nitrogen was then gradually replaced with hydrofluoric acid, care being taken that the increase in temperature did not exceed 95° C. and, when an HF/N₂ molar ratio of 50/50 was reached, the temperature was raised to 300° C.

After disappearance of the exothermic peaks the temperature was raised to 350° C. under a stream of pure hydrofluoric acid (1mol/hour) for 15 hours.

The catalyst was finally purged in a stream of nitrogen before the catalyst test is commenced. The characteristics of catalyst D dried and activated in this way were as follows:

| Chemical composition (by weight) | |
|---|---|
| fluorine: | 26.9% |
| chromium: | 53.3% |
| oxygen: | 19.8% (remainder to 100) |
| Physical properties: | |
| BET surface: | 101 m²/g |
| volume of pores with a radius of between 4 nm and 63 μm: | 0.13 cm³/g |
| surface of pores of radius greater than 4 nm: | 35.9 m²/g. |

The operating conditions and the results obtained with this catalyst D in the fluorination, at atmospheric pressure, of F115 present in the same crude F125 as in Example 1B are collated in Table 4, which follows:

TABLE 4

| TEST No. | 41 | 42 | 43 |
|---|---|---|---|
| Operating conditions | | | |
| Temperature (°C.) | 450 | 450 | 400 |
| HF/F115 + F125 molar ratio | 1 | 1 | 1 |
| Contact time(s) | 24 | 100 | 95 |
| Age of the catalyst (h) | 19 | 41 | 108 |
| Results | | | |
| Overall degree of conversion of F115 (%) | 90.3 | 100 | 91.6 |
| Selectivity for F116 (%) | ~100 | ~100 | ~100 |
| Overall degree of conversion of F125 (%) | 1.3 | 2.5 | 1 |
| F115 content in purified F125 (mol %) | 0.15 | traces | 0.13 |

We claim:

1. Process for the purification of a crude pentafluoroethane containing chloropentafluoroethane, comprising subjecting the crude pentafluoroethane to gas phase catalytic fluorination with HF at a temperature between 380 and 480° C. for 15 to 200 seconds, the molar ratio of HF/pentafluoroethane and chloropentafluoroethane being between 0.6 and 5, to selectively convert chloropentafluoroethane to hexafluoroethane, and then isolating the hexafluoroethane formed whereby substantially all of said chloropentafluoroethane is converted to hexafluoroethane.

2. Process according to claim 1, wherein the hexafluoroethane formed is isolated by distillation.

3. Process according to claim 1, wherein the fluorination is performed at a pressure ranging from 0 to 25 bars gauge.

4. Process according to claim 3, wherein the fluorination is performed in the presence of oxygen.

5. Process according to claim 3, wherein a mixed catalyst is employed which is based on nickel and chromium oxides, halides, and/or oxyhalides which are deposited on a support consisting of aluminum fluoride or of a mixture of aluminum fluoride and alumina.

6. Process according to claim 3, wherein a bulk $Cr_2O_3$ or Ni-Cr catalyst is employed.

7. Process according to claim 3, wherein the pressure is atmospheric pressure.

8. Process according to claim 1, wherein the molar content of chloropentafluoroethane in said crude pentafluoroethane is less than or equal to 30 mole %.

9. Process according to claim 1, wherein the molar content of chloropentafluoroethane in said crude pentafluoroethane is less than or equal to 10 mole %.

10. Process for the purification of a crude pentafluoroethane containing chloropentafluoroethane, comprising catalytically fluorinating the crude pentafluoroethane containing less than or equal to 30 mole % chloropentafluoroethane with a bulk $Cr_2O_3$ or Ni-Cr catalyst at a temperature between 380 and 480° C. for 15 to 200 seconds and at a mole ratio HF/pentafluoroethane and chloropentafluoroethane between 0.6 and 5 to selectively convert chloropentafluoroethane to hexafluoroethane, and then isolating the hexafluoroethane formed whereby substantially all of said chloropentafluoroethane is converted to a hexafluoroethane.

* * * * *